United States Patent [19]

Moeller et al.

[11] Patent Number: 5,662,912

[45] Date of Patent: Sep. 2, 1997

[54] SUGAR MONOACID AMIDES IN COSMETIC PREPARATIONS

[75] Inventors: Hinrich Moeller, Monheim; Rolf Wachter, Duesseldorf, both of Germany

[73] Assignee: Henkel Kommanditgesellschaft auf Aktien, Duesseldorf, Germany

[21] Appl. No.: 672,901

[22] Filed: Jun. 28, 1996

[30] Foreign Application Priority Data

Jun. 28, 1995 [DE] Germany ............ 195 23 479.0

[51] Int. Cl.$^6$ .................. A61K 7/48; A61K 7/06
[52] U.S. Cl. .................. 424/401; 424/101; 424/47; 514/547; 514/549; 514/844; 514/845; 514/846; 514/847
[58] Field of Search .................. 424/401, 707, 424/47; 514/547, 549, 844, 845, 846, 847

[56] References Cited

U.S. PATENT DOCUMENTS

| | | | |
|---|---|---|---|
| 5,208,355 | 5/1993 | Scott | 554/37 |
| 5,368,857 | 11/1994 | Corcoran et al. | 424/401 |
| 5,476,671 | 12/1995 | Cho et al. | 424/70.1 |

FOREIGN PATENT DOCUMENTS

| | | |
|---|---|---|
| 227 994 | 7/1987 | European Pat. Off. . |
| 277 641 | 8/1988 | European Pat. Off. . |
| 482 860 | 4/1992 | European Pat. Off. . |
| 495 624 | 7/1992 | European Pat. Off. . |
| 90/01323 | 2/1990 | WIPO . |

OTHER PUBLICATIONS

C.R. 23rd. CED Congress, Barcelona, 1992, p. 29.
Cosm.Toil. 107 45 (1992).
J.Soc. Cosmet. 40, 273 (1989).
S.E. Friberg, J.Soc.Cosmet. Chem. 41, 155 (1990).
EP 455429 (Nov. 6, 1991) Abstract.

*Primary Examiner*—Jyothsna Venkat
*Attorney, Agent, or Firm*—Ernest G. Szoke; Wayne C. Jaeschke; Real J. Grandmaison

[57] ABSTRACT

The invention relates to the use of acylated sugar monoacid amides in cosmetic preparations corresponding to formula I:

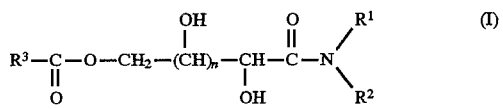

10 Claims, No Drawings

SUGAR MONOACID AMIDES IN COSMETIC PREPARATIONS

BACKGROUND OF THE INVENTION

1. Field of the Invention

This invention relates to the use of acylated sugar monoacid amides in cosmetic preparations, more especially skin-care and hair-care formulations.

2. Discussion of Related Art

A balanced water content in the individual layers of skin plays an important part in regard to the elasticity and appearance of the skin. The content of bound water is at its greatest in the dermis and in the boundary layer of the epidermis near the basal membrane. The elasticity of the skin is critically determined by the collagen fibrils in the dermis, the specific conformation of the collagen being achieved through the incorporation of water molecules. Destruction of the lipid barrier in the stratum corneum (SC), for example by surfactants, leads to an increase in the transepidermal water loss so that the water-containing surroundings of the cells are destroyed. Since the water bound in deeper layers of skin can only be supplied through vessels via the body fluid and not from outside, it is clear that maintenance of the barrier function of the stratum corneum is essential to the overall condition of the skin [cf. S. E. Friberg et al., *C. R. 23rd. CED Congress*, Barcelona, 1992, page 29].

Ceramides are lipophilic amides of long-chain fatty acids which are generally derived from sphingosine or phytosphingosine. This class of body fats has acquired considerable significance since they were discovered in the intercellular space between the corneocytes as key components for the buildup of the lipid bilayer, i.e. the permeability barrier, in the stratum corneum of human skin. Ceramides have molecular weights of well below 1,000 so that, when externally applied in a cosmetic formulation, they are able to reach the required point of action. The external application of ceramides results in restoration of the lipid barrier so that the above-mentioned disturbances to the skin function can be causally counteracted [cf. R. D. Petersen, *Cosm. Toil.* 107, 45 (1992)].

Hitherto, limits have been imposed on the use of ceramides on account of their inadequate availability. Accordingly, attempts have already been made to synthesize ceramide analogs, so-called synthetic barrier lipids (SBL) or pseudoceramides, and to use them for skin care [cf. G. Imokawa et al., *J. Soc. Cosmet. Chem.* 40, 273 (1989)].

For example, EP-A 0 277 641 and EP-A 0 227 994 (Kao) describe ceramide analogs with the following structure:

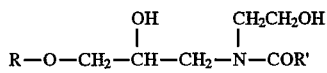

EP-A 0 482 860 and EP-A 0 495 624 (Unilever) describe ceramide-related structures corresponding to the following formula:

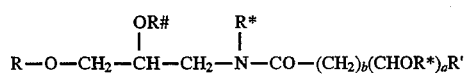

In addition, sugar derivatives with the following composition:

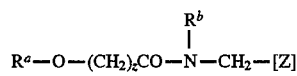

in which $R^a$ is hydrogen or an unsaturated fatty acyl group, z is a number of 7 to 49, $R^b$ is a hydroxyalkyl group and Z is a sugar or phosphate group, are proposed in EP-A 0 455 429 (Unilever) for the protection of skin and hair.

Japanese patent application J7 4043-935 describes acylated N-alkyl-D-gluconamides with the following structure:

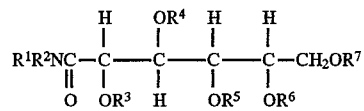

which are added to resins to improve their flowability, their demoldability or mold release and their electrostripping.

In spite of these various efforts, the results obtained with these substances have so far been unsatisfactory. In particular, the performance level of natural ceramides has never been matched. In addition, the synthesis sequences are technically complicated and therefore expensive which makes the significance of the substances even more relative.

The problem addressed by the present invention was to provide new high-performance ceramide analogs which would be distinguished by a simple synthesis. Another problem addressed by the invention was to provide new compounds based on non-animal raw materials with a structure which would be very close to the ceramides or pseudoceramides.

DESCRIPTION OF THE INVENTION

The present invention relates to the use of acylated sugar monoacid amides corresponding to formula I:

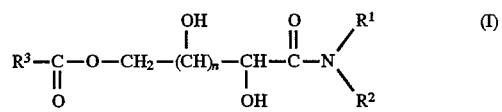

in which
$R^1$ and $R^3$ may be the same or different and, independently of one another, represent a linear or branched alkyl and/or alkenyl radical containing 6 to 30 carbon atoms or $R^1$ represents a group corresponding to formula II:

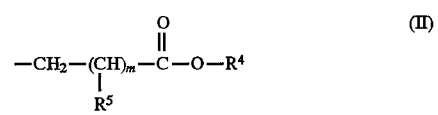

where
$R^4$ is a linear or branched alkyl and/or alkenyl radical containing 6 to 30 carbon atoms,
$R^5$ is hydrogen or a linear or branched alkyl or alkenyl radical containing 1 to 6 carbon atoms and
m is a number of 1 to 10,
$R^2$ represents hydrogen or an alkyl group containing 1 to 4 carbon atoms and
n may be a number of 0 to 4,
as a constituent of synthetic barrier lipids for the production of skin-care and hair-care formulations.

Acylated sugar monoacid amides corresponding to formula I, in which $R^1$ is octadecyl or docosyl, $R^3$ is hexadecyl or octadecyl and n is 3, are particularly preferred.

PRODUCTION PROCESS

The compounds corresponding to formula I may be obtained, for example, by acylation of uronic acid amides. The acylation may be carried out with fatty acids corresponding to the formula $R^3$—COOH, in which $R^3$ is as defined above, or reactive derivatives thereof, for example acid chlorides or fatty acid methyl esters. Where acid chlorides are used as the acylating agent, the reaction is preferably carried out in the presence of an acid binding agent at temperatures in the range from 0° to 100° C. and preferably at temperatures in the range from 18° to 60° C. Inert solvents, such as hydrocarbons, chlorinated hydrocarbons, ethers, such as t-butyl methyl ether, diethyl ether, tetrahydrofuran and 1,2-dimethoxyethane have proved to be suitable solvents. If fatty acid alkyl esters, for example fatty acid methyl ester, are used, the reaction is preferably carried out at elevated temperature, for example at a temperature of 80° C. to 160° C. and preferably at a temperature of 100° C. to 130° C., in the presence of alkaline catalysts. The acylation with fatty acid alkyl ester is preferably carried out without a solvent in the presence of a catalytic quantity of sodium methanolate or ethanolate, sodium or potassium hydroxide, sodium or potassium carbonate or potassium t-butanolate.

The uronic acid amides may be obtained in known manner by the aminolysis of sugar acid lactones or the lower alkyl esters of glyconic acids. In one particularly preferred embodiment, the amines may even be replaced by amino acid esters corresponding to general formula III:

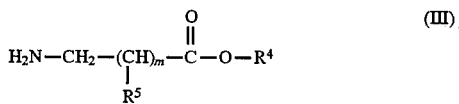

in which $R^4$, $R^5$ and m are as defined above.

COMMERCIAL APPLICATIONS

According to the invention, the compounds corresponding to formula I are used as a constituent of synthetic barrier lipids for the production of skin-care and hair-care formulations.

The acylated sugar acid amides to be used as synthetic barrier lipids in accordance with the invention strengthen the natural barrier function of the skin against external irritants. They improve the strength, suppleness and elasticity of the skin, increase its moisture content and protect it against drying out. At the same time, extremely fine wrinkles are smoothed.

However, special formulations which form liquid crystalline, lamellar structures are of particular advantage for maintaining the barrier function of the skin. In accordance with the composition of the horny layer lipids, these formulations may contain as their principal constituents from 5% by weight to 50% by weight of a compound corresponding to formula I, from 25% by weight to 75% by weight of saturated and unsaturated fatty acids, alkali metal salts thereof or mixtures of the fatty acids and salts thereof, from 10% by weight to 50% by weight of cholesterol, phytosterols and/or cholesteryl sulfate, 5% by weight to 30% by weight of triglycerides (triolein) and wax esters and from 2% by weight to 20% by weight of phospholipids, such as lecithins or cephalins. Typical examples of such formulations are skin creams, soft creams, nutrient creams, sun creams, night creams, skin oils, care lotions and body aerosols.

The compounds corresponding to formula I may be present in skin-care formulations both as water-in-oil and as oil-in-water emulsions in quantities of 1 to 50% by weight, preferably in quantities of 1 to 30% by weight and more preferably in quantities of 2 to 10% by weight, based on the formulation. PIT emulsions and microemulsions and also liposomal or lamellar liquid-crystalline dispersions may also serve as cosmetic carrier systems. Other typical auxiliaries and additives may be present in quantities of 5 to 95% by weight and preferably in quantities of 10 to 80% by weight. In addition, the formulations may contain water in a quantity of up to 99% by weight and preferably in a quantity of 5 to 80% by weight.

Carrier oils suitable for this purpose are, for example, mineral oils, vegetable oils, silicone oils, fatty acid esters, dialkyl ethers, fatty alcohols and Guerbet alcohols. Suitable emulsifiers are, for example, sorbitan esters, monoglycedes, polysorbates, polyethylene glycol monofatty acid/difatty acid esters, highly ethoxylated fatty acid esters, fatty alkyl polyglucosides and high molecular weight silicone compounds such as, for example dimethyl polysiloxanes with an average molecular weight in the range from 10,000 to 50,000. Other additives include preservatives, for example p-hydroxy-benzoic acid ester; antioxidants, for example butyl hydroxytoluene, tocopherol; humectants, for example glycerol, sorbitol, 2-pyrrolidine-5-carboxylate, dibutyl phthalate, gelatine, polyglycols with an average molecular weight of 200 to 600; buffers, for example lactic acid/TEA or lactic acid/NaOH; mild surfactants, for example alkyl oligoglucosides, fatty alcohol ether sulfates, fatty acid isethionates, taurides and sarcosinates, ether carboxylic acids, sulfosuccinates, protein hydrolyzates and fatty acid condensates, sulfotriglycerides, short-chain glucamides; phospholipids, waxes, for example beeswax, ozocerite wax, paraffin wax; plant extracts, for example extracts of Aloe vera; thickeners; dyes and perfumes and sun blocks, for example ultrafine titanium dioxide or organic substances, such as p-aminobenzoic acid and esters thereof, ethyl hexyl-p-methoxycinnamic acid ester, 2-ethoxyethyl-p-methoxycinnamic acid ester, butyl methoxydibenzoyl methane and mixtures thereof.

In one preferred embodiment of the invention, the acylated sugar acid amides, optionally in admixture with natural ceramides or pseudoceramides, may be mixed with cholesterol, cholesterol fatty acid esters, fatty acids, triglycerides, cerebrosides, phospholipids and similar substances to form liposomes or lamellar liquid crystalline structures.

In another preferred embodiment of the invention, the acylated sugar acid amides may be mixed with active-substance accelerators, more especially with ethereal oils, for example eucalyptus oil, menthol and the like.

Finally, in a third preferred embodiment, the acylated sugar acid amides may also be dissolved in squalene or squalane and, optionally with the other ingredients mentioned, may be formulated together with volatile or non-volatile silicone compounds as water-free or substantially water-free single-phase systems. Further examples of constituents and typical compositions can be found, for example, in WO 90/01323 (Bernstein) and S. E. Friberg, *J. Soc. Cosmet. Chem.* 41,155 (1990).

The acylated sugar acid amides may be present in hair-care formulations, such as shampoos, rinses, colorants and waving formulations, in quantities of 0.1 to 50% by weight, preferably in quantities of 1 to 30% by weight and more preferably in quantities of 2 to 10% by weight, based on the formulation. The hair-care formulations may contain as further auxiliaries and additives emulsifiers, superfatting agents, typical thickeners, biogenic agents, for example plant extracts, protein hydrolyzates and vitamin complexes, and typical preservatives. The dyes used may be any of the dyes suitable and permitted for cosmetic purposes, as listed for example in the publication entitled "*Kosmetische Färbemittel*" of the Farbstoffkommission der Deutschen Forschungsgemeinschaft, published by Verlag Chemie, Weinheim, 1984, pages 81 to 106. These dyes are normally used in concentrations of 0.001 to 0.1% by weight, based on the formulation as a whole. The total percentage content of auxiliaries and additives may be from 1 to 50% by weight and is preferably from 5 to 40% by weight, based on the formulation.

The following Examples are intended to illustrate the invention without limiting it in any way.

EXAMPLES

EXAMPLES 1

7.78 g (21.9 mmoles) of stearoyl chloride in 20 ml of THF were added dropwise at 30° C. to a stirred mixture of 10 g (19.9 mmoles) of N-behenyl-D-gluconamide and 2.22 g (21.9 mmoles) of triethylamine in 150 ml of tetrahydrofuran (THF). The mixture was then stirred for 5 hours at that temperature and filtered, after which the solvent was distilled off under reduced pressure. The residue was triturated with a little petroleum ether, filtered and treated once more with petroleum ether. After filtration and drying, N-behenyl-D-gluconamide monostearic acid ester (Mp. 47°–58° C.) was obtained in a yield of 13.9 g (91% of the theoretical).

EXAMPLE 2

12.5 g of anhydrous potassium carbonate was added to a mixture stirred at 110° C. of 219 g (0.5 mole) of N-octadecyl-D-gluconamide and 1072 g (5.0 moles) of methyl laurate and the whole was uniformly heated for 2 hours to 135° C., methanol distilling off. After cooling to 115° C., the reaction mixture was neutralized to pH 6.4 with 14.8 g of concentrated phosphoric acid and excess methyl laurate was distilled off in an oil pump vacuum to a sump temperature of 140° C. Yellowish wax-like N-octadecyl-D-gluconamide monolauric acid ester was obtained in a yield of 305 g (around 90% of the theoretical).

What is claimed is:

1. A skin-care or hair-care composition containing acylated sugar monoacid amides corresponding to formula I $$R^3-\underset{\underset{O}{\|}}{C}-O-CH_2(CH)_n\underset{\underset{OH}{|}}{CH}-\underset{\underset{}{\|}}{\overset{O}{C}}-N\overset{R^1}{\underset{R^2}{\diagdown}} \quad (I)$$

in which $R^1$ and $R^3$ may be the same or different and, independently of one another, represent a linear or branched alkyl or alkenyl radical having 6 to 30 carbon atoms or $R^1$ represents a group corresponding to formula II:

$$-CH_2-(CH)_m\underset{\underset{R^5}{|}}{\overset{\overset{O}{\|}}{C}}-O-R^4 \quad (II)$$

where $R^4$ is a linear or branched alkyl or alkenyl radical having 6 to 30 carbon atoms, $R^5$ is hydrogen or a linear or branched alkyl or alkenyl radical having 1 to 6 carbon atoms and m is a number of 1 to 10, $R^2$ represents hydrogen or an alkyl group having 1 to 4 carbon atoms and n may be a number of 0 to 4.

2. A composition as in claim 1 wherein said amides corresponding to formula I are present in a quantity of 1% to 50% by weight, based on the weight of said composition.

3. A composition as in claim 1 further containing ceramides, pseudo-ceramides, cholesterol, cholesterol fatty acid esters, fatty acids, triglycerides, cerebrosides, or phospholipids.

4. A composition as in claim 1 further containing essential oils selected from the group consisting of eucalyptus oil and menthol.

5. A composition as in claim 1 wherein said amides corresponding to formula I are present in the form of a solution in squalene or squalane.

6. A cosmetic composition containing a synthetic barrier lipid comprising acylated sugar monoacid amides corresponding to formula I:

$$R^3-\underset{\underset{O}{\|}}{C}-O-CH_2(CH)_n\underset{\underset{OH}{|}}{CH}-\underset{\underset{}{\|}}{\overset{O}{C}}-N\overset{R^1}{\underset{R^2}{\diagdown}} \quad (I)$$

in which $R^1$ and $R^3$ may be the same or different and, independently of one another, represent a linear or branched alkyl or alkenyl radical having 6 to 30 carbon atoms or $R^1$ represents a group corresponding to formula II:

$$-CH_2-(CH)_m\underset{\underset{R^5}{|}}{\overset{\overset{O}{\|}}{C}}-O-R^4 \quad (II)$$

where $R^4$ is a linear or branched alkyl or alkenyl radical having 6 to 30 carbon atoms, $R^5$ is hydrogen or a linear or branched alkyl or alkenyl radical having 1 to 6 carbon atoms and m is a number of 1 to 10, $R^2$ represents hydrogen or an alkyl group having 1 to 4 carbon atoms and n may be a number of 0 to 4.

7. A cosmetic composition as in claim 6 wherein said amides corresponding to formula I are present in a quantity of 1% to 50% by weight, based on the weight of said composition.

8. A cosmetic composition as in claim 6 further containing ceramides, pseudo-ceramides, cholesterol, cholesterol fatty acid esters, fatty acids, triglycerides, cerebrosides, or phospholipids.

9. A cosmetic composition as in claim 6 further containing essential oils selected from the group consisting of eucalyptus oil and menthol.

10. A cosmetic composition as in claim 6 wherein said amides corresponding to formula I are present in the form of a solution in squalene or squalane.

* * * * *